United States Patent [19]

Roche

[11] Patent Number: 5,075,114

[45] Date of Patent: Dec. 24, 1991

[54] TASTE MASKING AND SUSTAINED RELEASE COATINGS FOR PHARMACEUTICALS

[75] Inventor: Edward J. Roche, Hawthorne Place, Pa.

[73] Assignee: McNeil-PPC, Inc., Milltown, N.J.

[21] Appl. No.: 528,003

[22] Filed: May 23, 1990

[51] Int. Cl.$^5$ .............................................. A01J 21/00
[52] U.S. Cl. .................................. 424/470; 424/464; 424/468; 424/469; 424/472; 514/617; 514/960
[58] Field of Search ............... 514/617, 960; 424/468, 424/472, 469, 470

[56] References Cited

U.S. PATENT DOCUMENTS

| | | | |
|---|---|---|---|
| 4,606,909 | 8/1986 | Bechgaard | 424/469 |
| 4,643,892 | 2/1987 | Peters | 514/617 |
| 4,800,087 | 1/1989 | Mehta | 424/497 |
| 4,835,187 | 5/1989 | Reuter et al. | 514/570 |
| 4,835,188 | 5/1989 | Ho et al. | 514/570 |
| 4,837,031 | 6/1989 | Denton | 424/464 |
| 4,851,226 | 7/1989 | Julian | 424/470 |
| 4,894,233 | 1/1990 | Sharma | 514/960 |
| 4,900,558 | 2/1990 | Barry | 424/470 |
| 4,915,949 | 4/1990 | Wong | 424/468 |
| 4,915,953 | 4/1990 | Jordan | 424/472 |

FOREIGN PATENT DOCUMENTS 2166651A  5/1986  United Kingdom .

*Primary Examiner*—Thurman K. Page
*Assistant Examiner*—William E. Benston, Jr.
*Attorney, Agent, or Firm*—Joseph J. Brindisi

[57] ABSTRACT

Chewable medicament tablets are made from coated granules of a medicament wherein the coating on said granules comprises a blend of cellulose actate and/or cellulose acetate butyrate and hydroxypropyl cellulose and a process for making such tablets and a method of providing sustained release of medicaments utilizing such coated granules in a tablet.

19 Claims, No Drawings

TASTE MASKING AND SUSTAINED RELEASE COATINGS FOR PHARMACEUTICALS

FIELD OF THE INVENTION

This invention relates to tablets containing means to mask the taste of active ingredients and/or provide sustained release of such ingredients. More particularly, the means of providing taste masking and/or sustained release of active ingredients are coatings comprising blends of hydroxypropyl cellulose with cellulose acetate and/or cellulose acetate butyrate.

BACKGROUND OF THE INVENTION

Orally administered medicaments are given to the patient in many forms, such as liquid solutions, emulsions, or suspensions, or in solid form such as capsules or tablets (as used herein, the term "tablet" means any shaped and compressed solid dosage form, including caplets). Medicaments administered in tablet or capsule form are usually intended to be swallowed whole. Therefore, the often disagreeable taste of the active ingredient need not be taken into account in formulating the medicine, except for the provision of means to prevent the taste from being apparent during the short time that the medicine is in the mouth. Such means may include the provision of an appropriately thin and quickly dissolving coating on the tablet, the use of the gelatin capsule form (the gelatin outer shell of the capsule keeps the active ingredient inside until the capsule has been swallowed), or simply compressing a tablet firmly so that it will not begin to disintegrate during the short time that it is intended to be in the mouth.

Children, older persons, and many other persons have trouble swallowing whole tablets and even capsules. Therefore, in cases where the dosage to be administered cannot be made into a very small tablet or capsule, it is desirable to provide the medicine either in liquid form or in a chewable solid form, in addition to the tablet or capsule that is designed to be swallowed whole. Even where the medicine can be formulated as a liquid, it is desirable also to be able to provide a chewable solid form because it is usually more convenient to carry a supply of tablets with oneself all day than a container of liquid medicine.

A common problem with chewable tablet forms is the often disagreeable taste of the active ingredient which manifests itself during chewing. In some cases, the taste of the active medicament in a tablet can be overpowered by adding flavoring ingredients to the tablet so that when it is chewed the taste of the active ingredient is simply overpowered. For instance, this has been done with children's aspirin where the dosage is small enough so that the amount of flavoring agents needed to mask the taste of the medicine is not so great that the tablet becomes unreasonably large. A children's size tablet of acetaminophen (acetyl para-aminophenol or "APAP") is available commercially wherein the APAP is present in, granules that are coated with ethyl cellulose. A significant proportion of the APAP remains shielded by the coating (and therefore does not contribute to taste) while the tablet is in the mouth, despite some breakage of the ethyl cellulose coating during compression of the tablet and some additional breakage of the coating during chewing. The APAP becomes bioavailable via permeation through the coating (although ethyl cellulose is not soluble in aqueous fluids, water does permeate through the coating) and from the granules wherein the coating was broken.

Co-pending U.S. Pat. application Ser. No. 214,265 filed June 30, 1988 as a continuation-in-part application of Ser. No. 121,692 filed Nov. 16, 1987, now abandoned, by Thomas N. Julian and Galen W. Radebaugh discloses chewable medicament tablets wherein the granules of active ingredient are coated with a blend of cellulose acetate or cellulose acetate butyrate and polyvinyl pyrrolidone (PVP).

The present invention is directed to the discovery of a coating that can be used to coat granules of active medicament and which can achieve a better balance between taste masking and control of bioavailability than can be achieved with ethyl cellulose or other previously known combinations. Further, the coating of the invention can provide a sustained release coating for medicaments.

SUMMARY OF THE INVENTION

As embodied and fully described herein the present invention provides a medicament coating comprising a blend of cellulose acetate (CA) and/or cellulose acetate butyrate (CAB) and hydroxypropyl cellulose (HPC). The coating provides excellent taste masking while still permitting acceptable bioavailability of the active ingredient. Further, the coating can provide for sustained release of the medicament.

In preferred embodiments of the invention the coated medicament is included in a chewable tablet comprising compressed individual particles of medicament particles coated with a blend of CA and/or CAB and HPC.

In further preferred embodiments, ibuprofen particles are coated with a blend of CA and/or CAB and HPC and are then compressed into tablet form together with flavoring agents and other ingredients that are customarily used in making such chewable tablets.

The invention also provides a process of making and methods using the chewable tablets, as well as, a method of using the coated medicament particles for sustained release of the active ingredients.

DETAILED DESCRIPTION OF THE INVENTION

The invention will now be described specifically in terms of its most preferred embodiments which is the preparation of chewable tablets of ibuprofen, a medicament used in both over-the-counter preparations and in prescription drugs for analgesic and antipyretic purposes. Reference will also be made in detail herein to other preferred embodiments of the compositions, processes and methods of the invention.

In the preferred embodiment of the process of the invention, medicament, preferably ibuprofen in granular form, is coated with a blend of HPC and CA and/or CAB so that the granules are coated with the polymer blend. The coated granules, together with other ingredients such as flavoring agents, extenders, exipients, and the like, are compressed into tablet form. (As used herein, the term "granule" refers to individual particles or to agglomerates of individual Particles of the medicament.) A high enough proportion of the coating remains effectively intact on the ibuprofen granules through the compression of the tablet and through normal chewing in the mouth to permit effective taste masking of the normally bitter tasting ibuprofen. The term "effectively intact" means that the coating remains sufficiently integral to mask the taste or flavor of the medicament detectable through the coating. This taste masking provides a mean to limit the quantity of other flavoring agents in the tablet is not be so large that an excessively large tablet is required to overpower rather than mask the unpleasant flavor of the medicament.

When the coated granules are swallowed, the active medicament becomes bioavailable via permeation through the coating. Permeation can occur through the intact coating as well as through the coating that has become porous through dissolution of the water soluble HPC component of the coating; the CA and CAB components are water insoluble. Permeation also occurs via disintegration of the coating, which is caused in part by chewing, in part by processing of the tablet (compression), and in part by removal of the HPC component of the coating by dissolution.

The coating may be designed so that the medicament is released relatively rapidly or in a sustained release mode, depending on the proportion of coating to medicament in the granules, or the proportion of the CA and/or CAB to HPC in the coating, or their combination. Generally, higher proportions of HPC used in the coating leads to more rapid release of the medicament.

Cellulose acetate and cellulose acetate butyrate are quite water insoluble but are soluble in organic solvents. They can provide good taste masking properties since they do not dissolve in the mouth and are tough enough to remain effectively intact during processing and normal chewing in the mouth. If used alone, however, a coating of CA and/or CAB would not provide adequate bioavailability of the active ingredient after swallowing the chewed tablet. To provide the requisite bioavailability, HPC is added. HPC is a polymer which is soluble in both water and organic solvents. The water solubility of HPC provides the bioavailability of the active medicament in the GI tract via the mechanisms discussed above. The solubility of HPC in organic solvents permits ready mixing with CA or CAB during the production of the coated granules, since CA and CAB are not very soluble, if at all, in water, and are most conveniently applied from an organic solvent solution. HPC and CA and/or CAB form clear compatible solutions in organic solvents, preferably acetone/methanol mixtures, which are suitable for pharmaceutical coating. The blend of CA and/or CAB and HPC provides the balance needed for good taste masking while being chewed in the mouth, along with either rapid or sustained bioavailability of the active medicament in the GI tract after swallowing.

The HPC and CA and/or CAB blends of the invention have been found to be more versatile than the PVP blends of Julian and Radebaugh discussed earlier. Due to the superior flexibility of HPC polymer as compared to PVP, higher percentages of HPC (up to 50%) can be used than is recommended by Julian and Radebaugh for PVP (3 to 30%). Higher amounts of the water soluble component HPC increases the rate and extent of disintegration of the coating thus increasing the porosity of the coating. Presence of such higher amount of the water soluble component HPC advantageously increases the bioavailability of the coated medicaments.

The coating used is preferably a blend containing about 50 to about 97 percent of CA and/or CAB, by weight of the coating, and about 3 to about 50 percent HPC. Within the range indicated, if sustained release of the medicament is desired, a lower proportion of the water soluble HPC may be used. When rapid release of the medicament is desired, a higher proportion of the water soluble HPC is used, i.e. up to 50 percent. Routine experimentation will suffice to determine the appropriate proportions of the two polymers to use in individual cases, as is more specifically illustrated below. The upper limit of about 50 percent HPC is limited by practical processing considerations. The tackiness of the coating solution increases in the higher range amounts of HPC and amounts over 50 percent may lead to particle agglomeration during the coating process. Further, the rate of release can be controlled by use of HPC of specific molecular weight, whereby, higher molecular weight HPC leads to a slower release of medicament.

The coated granules may be made by coating the granules of medicament with an organic solvent solution of the polymers in a fluidized bed coating operation. A wide variety of organic solvents may be used to prepare the organic solvent solution of the coating polymers. For instance, a preferred solvent is acetone-methanol, but other solvent systems may also be used, including methylene chloride-methanol (e.g. 9:1), acetone-ethyl acetate, toluene-ethanol, and others. As a general rule, the proportion of polymer in the solvent solution will be from about 5 to 20 and preferably 8 to 15 weight percent for optimal taste masking and rapid release of drug depending upon the specific solvents used and other similar considerations.

The polymers are dissolved in the solvent and the polymer solution is then coated onto ibuprofen or other medicament active ingredient or combination of ingredients granules, using a fluidized bed coater. Air (which may be heated) passes through a bed of the medicament granules to fluidize them, and the solvent solution of the two polymers is sprayed onto the fluidized bed and thereby coats the granules. The air passing through the bed dries the coated granules, so that a dry coated granule is obtained. The coated granules are then used in combination with various excipients, flavors, and colors to make a chewable tablet.

The dried coating as thus applied usually constitutes about 5-28 % of the total dry weight of the coated ibuprofen granule. The exact proportions of coating to medicament desired for individual cases can be determined by routine experimentation. The amount of coating may be varied in light of the intended application and desired bulk of the products. Chewable tablets can be acceptable in larger sizes than swallowed tablets since chewing will reduce the size of the tablets in the mouth. Further, tablets intended for pediatric use generally comprise reduced dosage amounts and less bulk. Larger proportions of coating may be used to provide a sustained release or better taste formulation.

When two or more medicaments are utilized in a tablet the coatings may be varied to provide a slower release of one medicament over another. This is especially advantageous for dosing a combination of medicaments that are more effectively released in different parts of the digestive tract or are better released separately in the digestive tract to avoid interference with each other or other incompatibility. Further, the same medicament may be subject to different coating composition and amounts to provide for sustained release of some portion of the medicament and immediate release of another portion of the medicament to achieve an optimal dosing versus time profile. Obtaining such optimal dosing/time profiles depends upon the particular medicaments and medical needs required. The exact proportions of coating materials used to achieve these profiles can be determined by routine experimentation.

While exact size of the coated granules has not been found to be critical, the coated granules will usually be sized to pass between between about a 10 and 200 mesh sieve screen (U. S. Sieve Series). In the usual case, the coated granules will be sized from about 40 to 60 mesh.

In addition to ibuprofen, any solid medication in need of taste masking can be used in the invention. Illustrative examples include aspirin, naproxen, acetaminophen, pseudoephedrine, substantially pure dexibuprofen (i.e. less than 20% of the inactive R-antipode), dexibuprofen lysine, cimetidine, ranitidine, nizatidine, psuedoephedrine hydrochloride, chlorpheniramine maleate, dextromethorphan hydrobromide, diphenhydramine hydrochloride or citrate, dextromethorphan, chlorpheniramine, loperimide, simethicone, salts thereof and combinations thereof. Identification of medicaments herein is intended to apply to pharmaceutically acceptable salts thereof as well. Further, the coating of the invention provides a convenient means for providing sustained release of medicaments and for presenting a viable dosage form for combination medicaments which are incompatible before (during storage) or after administration or for medicaments which are desirably released in the GI tract at various times or in various places thereof.

EXAMPLES

The following procedure and Examples provide examples of preferred method and materials for practicing the present invention. These Examples should be considered illustrative only and not limitative of the present invention.

An illustrative preferred procedure for preparing the coated granules of medicament in accordance with the invention is the following:

A solution of the coating polymers is prepared in an organic solvent by simply adding the polymers to the solvent with stirring. The medicament, in granular form, is placed in a fluidized bed coater and is fluidized by a flow of warm air. The temperature of the air has not been found to be narrowly critical, and can vary over a wide range, keeping in mind the fact that the temperature should not be high enough to cause decomposition, sintering, or melting of the medicament granules. When coating ibuprofen granules, a temperature of from about 55° to 75° C. is suitable but such temperature ranges will change depending on the medicament being coated. The rate of air flow is adjusted so as to fluidize the granules. Such flow will vary depending on factors such as the specific equipment used, the size of the charge of granules, the size of the individual granules, the apparent specific gravity of the granules, and other factors that are known to the worker in the arts relating to fluidized bed coating.

After the medicament has been fluidized, the polymer solution is sprayed on top of the fluidized bed. The air flow through the bed is continued until the amount of solvent remaining in the coating has been reduced to parts per million levels. The granules are actually dry to the touch within a very short time after the coating solution has been sprayed onto the granules of medicament; a matter of a few seconds in some cases. However, the total drying time required to ensure that the organic solvent content of the coating has been reduced to the level desired may take much longer, depending on the temperature of the air, the size of the batch, and the like. For batches of ibuprofen weighing four to six kilograms, total drying times of the order of one to three hours have been used. Routine experimentation will suffice to determine the appropriate air temperatures and total times required in the fluidized bed coaters in individual cases.

The Examples below set forth the ingredients and proportions for typical laboratory scale preparations of coated medicament granules. The materials used are the following:

Ibuprofen—In the form of granules having a particle size of about 60 mesh;

Loperamide (HCl salt)—In the form of granules having a particle size of about 40–80 mesh;

APAP—Acetaminophen USP granules having a particle size of about 170–270 microns;

Famotidine—In the form of granules having a particle size of about 170–270 microns;

Dexibuprofen lysine—substantially pure granules of S-ibuprofen lysine salt with less than 20 and preferably less than 10% of the inactive R-ibuprofen antipode present.

CA—Cellulose acetate NF powder, for example, CA 398-10 or CA-320S available from the Food and Pharmaceutical Products Division of FMC may be used. The CA 398-10 polymer has an acetyl content of about 39.8%, by weight, a hydroxyl content of 3.4%, by weight, a degree of substitution of 2.7, and a solution viscosity of about 38 poises or 10 seconds, determined by ASTM Method D 1343 in the solution described as Formula A, ASTM Method D 871. According to the manufacturer, the typical weight average molecular weight is 177,000 and the typical number average molecular weight is 58,500. The CA-320-S polymer has an acetyl content of about 32.0%, by weight, a hydroxyl content of about 9.0%, by weight, and a degree of substitution of 2.1. The manufacturer reports a solution viscosity in 90:10 $CH_2Cl_2$:methanol, at 4% (w/w) concentration, of 50 cps. Typical weight average molecular weight is 100,500 and typical number average molecular weight is 63,500, according to the manufacturer. (Viscosities in poises are converted to ASTM seconds equivalent to values obtained under ASTM Method D 871.);

CAT—Cellulose triacetate powder, CA-435-75S is also available from FMC. This CAT's acetyl content is 43.5 and the solution viscosity is 68 seconds, determined by the "Ball Drop Method" of ASTM D 1343, using the solution designated "Formula D" in Table 2 of ASTM D 871;

CAB—Cellulose acetate butyrate, CAB 171-15S from FMC. The polymer has a butyryl content of 17 weight percent, an acetyl content of 29.5 weight percent, and a viscosity of 24 cps in a 4 weight percent solution in methylene chloride:methanol (90:10) one day after solution preparation. The viscosity is taken at about 25° C.;

HPC—Hydroxypropyl cellulose having a molecular weight of about 80,000 to about 370,000. Suitable HPC includes those available from Aqualon in the grades known by the tradenames KLUCEL EF, LF, JF or GF.

The term "total coat" refers to the proportion of coating to medicament in the coated granule product, "charge" to the weight of medicament, "polymer solution" to the proportion of polymer in the organic solvent solution, and "total batch" to the weight of medicament plus coating.

Examples I-X, below, display the identity of medicament(s), coating polymers, organic solvents and organic solvent solutions of coating polymers, and the proportions of all of these materials for typical laboratory scale batches of coated medicament granules for use in the invention in accordance with the preferred procedure for preparing coated granules of medicament as described above.

EXAMPLE I

Active—Acetaminophen
Form of Active—Granular APAP with particle size of 170-270 microns.
Coating Solution—Cellulose Acetate 398-10/ Klucel LF in Acetone/Methanol 80/20 at 8-12% solids.
Note: Klucel LF has a weight average molecular weight of 95,000. Klucel EF (Molecular Weight 80,000) can also be used.
Blend Ratio
   70/30 to 90/10 (CA/HPC) for taste masking.
   85/15 to 97/3 for sustained release.
Coat Level
   10-15% for taste masking.
   16-28% for sustained release.

EXAMPLE II

Active—Acetaminophen
Form of Active—Rotogranulated APAP with smooth, approximately spherical shape. Size of 170-270 microns.
Otherwise same as above for I.

EXAMPLE III

Active—Famotidine
Form of Active—Rotogranulated with a carrier such as lactose which results in a smooth, approximately spherical shape. Binders such as povidone can be included in the Rotogranulated particles at levels of 1-10%. Same granular size as in I.
Coat Level 7-15% for taste masking.
Otherwise same as above for I.

EXAMPLE IV

Active-Dexibuprofen lysine (or other salts of ibuprofen such as Sodium Ibuprofen)
Form of Active—Rotogranulated particles can include a binder such as Povidone at levels of 1-10%. Granular size of 170-270 microns.
Coat Level: 10-18% for taste masking.

EXAMPLE V

Active—Naproxen Sodium
Form of Active—Rotogranulated as in Example IV.
Otherwise same as above for IV.

EXAMPLE VI

| Total Coat | 12% w/w | | |
|---|---|---|---|
| Charge | 4000 gms | ibuprofen | |
| Total Polymer | | | 545.45 gms |
| Polymer 1 | 65% w/w | CA | 354.54 gms |
| Polymer 2 | 10% w/w | CAB | 54.55 gms |
| Polymer 3 | 25% w/w | HPC | 136.36 gms |
| Polymer Soln | 10% w/w | | 5454.55 gms |
| Solvent 1 | 80% w/w | acetone | 3927.27 gms |
| Solvent 2 | 20% w/w | methanol | 981.82 gms |
| Total Batch | | 4545.45 gms | |

EXAMPLE VII

| Total Coat | 12% w/w | | |
|---|---|---|---|
| Charge | 4000 gms | ibuprofen | |
| | 480 gms | pseudoephedrine | |
| Total Polymer | | | 545.45 gms |
| Polymer 1 | 60% w/w | CA | 327.27 gms |
| Polymer 2 | 40% w/w | HPC | 218.18 gms |
| Polymer Soln | 8% w/w | | 6818.18 gms |
| Solvent 1 | 80% w/w | acetone | 5018.18 gms |
| Solvent 2 | 20% w/w | methanol | 1254.55 gms |
| Total Batch | | 5025.45 gms | |

EXAMPLE VIII

| Total Coat | 12% w/w | | |
|---|---|---|---|
| Charge | 4000 gms | APAP | |
| | 480 gms | pseudoephedrine | |
| | 32 gms | chlorpheniramine | |
| | 240 gms | dextromethorphan | |
| Total Polymer | | | 545.45 gms |
| Polymer 1 | 70% w/w | CA | 381.82 gms |
| Polymer 2 | 30% w/w | HPC | 163.63 gms |
| Polymer Soln | 10% w/w | | 5454.55 gms |
| Solvent 1 | 80% w/w | acetone | 3927.27 gms |
| Solvent 2 | 20% w/w | methanol | 981.82 gms |
| Total Batch | | 5297.45 gms | |

EXAMPLE IX

| Total Coat | 12% w/w | | |
|---|---|---|---|
| Charge | 4000 gms | aspirin | |
| Total Polymer | | | 545.45 gms |
| Polymer 1 | 85% w/w | CA | 463.64 gms |
| Polymer 2 | 15% w/w | HPC | 81.82 gms |
| Polymer Soln | 8% w/w | | 6818.18 gms |
| Solvent 1 | 90% w/w | acetone | 5645.45 gms |
| Solvent 2 | 10% w/w | ethyl acetate | 627.27 gms |
| Total Batch | | 4545.45 gms | |

EXAMPLE X

| Total Coat | 12% w/w | | |
|---|---|---|---|
| Charge | 4000 gms | loperamide HCl | |
| Total Polymer | | | 545.45 gms |
| Polymer 1 | 80% w/w | CA | 436.36 gms |
| Polymer 2 | 20% w/w | HPC | 109.09 gms |
| Polymer Soln | 8% w/w | | 6818.18 gms |
| Solvent 1 | 80% w/w | acetone | 5018.18 gms |
| Solvent 2 | 20% w/w | methanol | 1254.55 gms |
| Total Batch | | 4545.45 gms | |

EXAMPLE XI

| Total Coat | 12% w/w | | |
|---|---|---|---|
| Charge | 4000 gms | APAP | |
| Total Polymer | | | 545.45 gms |
| Polymer 1 | 85% w/w | CAB | 463.64 gms |
| Polymer 2 | 15% w/w | HPC | 81.82 gms |
| Polymer Soln | 8% w/w | | 6818.18 gms |
| Solvent 1 | 80% w/w | $CH_2Cl_2$ | 5018.18 gms |
| Solvent 2 | 20% w/w | methanol | 1254.55 gms |
| Total Batch | | 4545.45 gms | |

EXAMPLE XII

Various other medicament combinations are prepared by coating desirable dosage ranges of medicaments cimetidine, ranitidine and nizatidine and combinations of two or more of pseudeuphedrine HCl, chlorpheniramine maleate, dextromethorphan HBr, diphenhydramine HCl or citrate, acetaminophen, ibuprofen and naproxen in accordance with the procedure and coatings of any of Examples I-XI While the use of fluidized bed coating has been described in some detail as one preferred method for making the coated granules that are utilized in the invention, other techniques for making the coated granules may be used. Such other techniques include various microencapsulation techniques such as coacervation and solvent evaporation.

The following examples XI-XIV describes preparation of chewable tablets.

EXAMPLE XIII

The ingredients displayed below, are sieved, dry blended, and compressed by standard procedures into round (disc shaped) chewable tablets, each weighing 1100 milligrams. The tablets had diameters of 9/16 inch, thicknesses of 0.573 centimeter, and had volumes of 0.919 cubic centimeter. Each tablet contained 200 milligrams of active ibuprofen per tablet, from coated granules prepared in accordance with the procedure of Example 1 containing 15 weight percent coating in which the proportion of CA:HPC was 85:15% w/w. The table below displays the ingredients, mg/tablet, percent, and grams/batch sufficient to make 10,000 tablets.

| Component | mg/Tablet | Percent | Gms/Batch |
|---|---|---|---|
| mannitol | 611.79 | 64.75 | 6117.94 |
| AVICEL PH101 | 71.76 | 7.59 | 717.65 |
| aspartame | 11.84 | 1.25 | 118.41 |
| citric acid (anhyd) | 5.74 | 0.61 | 57.41 |
| flavor | 4.31 | 0.46 | 43.06 |
| PROSWEET | 2.87 | 0.30 | 28.71 |
| Mg stearate | 9.33 | 0.98 | 93.29 |
| coated ibuprofen | 227.27 | 24.05 | 2272.70 |

The following table displays some typical proportion ranges for the ingredients that were used in Examples XIII:

TABLE

| Component | Range of Proportions, % |
|---|---|
| mannitol | 30-70 |
| AVICEL PH101 | 5-12 |
| aspartame | 0.5-3 |
| citric acid | 0.1-2 |
| flavor | 0.2-2 |
| PROSWEET | 0.1-2 |
| mg stearate | 0.4-2 |
| coated ibuprofen | 10-50 |

The functions of the several ingredients and some typical replacements for them are as follows:

Mannitol is a sweetener. It can be replaced by dextrose, fructose, sorbitol, compressible sugar, or lactose;

Avicel PH101 is microcrystalline cellulose. It is used as a tabletting aid, e.g. to impart hardness. It may be replaced with tricalcium phosphate;

Aspartame is an artificial sweetener. It can be replaced with others such as saccharin;

Citric acid is used as an acidifying agent to enhance the taste. It can be replaced by other acidifying agents such as malic acid;

The flavoring agent can be any flavoring agents such as vanilla, peppermint, orange, cherry, or spearmint;

Prosweet is another sweetener. It can be replaced with other materials such as saccharin, aspartame, natural sugars; and Magnesium stearate is a lubricant (to lubricate the dye walls and punches used during the tablet compression procedure). It can be replaced by talc, stearic acid, calcium stearate, zinc stearate, or the like.

The scope of the present invention is not limited by the description, examples and suggested used herein and modifications can be made without departing from the spirit of the invention. For example, other components may be added to the tablets including additional actives, various flavorings, preservatives and other pharmaceutical excipients. The present invention may also be used to provide a sustained release and/or chewable form for vitamins, minerals or other nutrients.

Application of the compositions and processes of the present invention for medical and pharmaceutical uses can be accomplished by any clinical, medical and pharmaceutical methods and techniques as are presently and prospectively known to those skilled in the art. Thus it is intended that the present invention cover the modifications and variations of this invention provided that they come within the scope of the appended claims and their equivalents.

What is claimed is:

1. A chewable tablet of a medicament comprising compressed coated granules, said coated granules individually comprising medicament coated with from about 5 to about 28% of the total dry weight of the coated medicament granule of a polymer blend of: (a) cellulose acetate, cellulose acetate butyrate and combinations thereof; and (b) hydroxypropyl cellulose wherein the ratio of cellulose acetate, cellulose acetate butyrate and combinations thereof to hydroxypropyl cellulose is in the range of about 97/3 to about 50/50.

2. The chewable tablet of claim 1 wherein the medicament is selected from the group consisting of ibuprofen, acetaminophen, aspirin, naproxen, pseudoephedrine, dextromethorphan, chlorpheniramine, loperamide, diphenhydramine, famotidine, cimetidine, ranitidine, nizatidine, salts thereof, and combinations thereof.

3. The chewable tablet of claim 1 wherein the polymer blend is intended for sustained release and contains from about 3 to about 15 weight percent of hydroxypropyl cellulose.

4. The chewable tablet of claim 1 wherein the coated granules are intended for sustained release and contain from about 16 to about 28 percent of said polymer blend.

5. The chewable tablet of claim 1 wherein the coated granules are intended for taste mask and contain from about 8 to about 15 weight percent of the polymer blend.

6. The chewable tablet of claim 1 wherein the medicament comprises ibuprofen.

7. The chewable tablet of claim 1 wherein the medicament comprises dexibuprofen lysine.

8. The chewable table of claim 1 wherein the medicament comprises ibuprofen.

9. The chewable table of claim 1 wherein the medicament comprises a combination of ibuprofen and pseudoephedrine.

10. The chewable table of claim 1 wherein the medicament comprises loperamide.

11. The chewable tablet of claim 1 wherein the medicament comprises acetaminophen and diphenhydramine hydrochloride or citrate.

12. The chewable tablet of claim 1 wherein the medicament comprises a combination of acetaminophen, pseudoephedrine, dextromethorphan and chlorpheniramine.

13. The chewable tablet of claim 1 wherein the medicament is a combination of an analgesic selected from the group consisting of ibuprofen, acetaminophen and aspirin; with pseudoephedrine; chlorpheniramine, and dextromethorphan.

14. A process of preparing a chewable medicament tablet comprising the steps of:
coating medicament granules with from about 5 to about 28% of the total dry weight of the coated medicament granule with a polymer blend of cellulose acetate, cellulose acetate butyrate or a combination thereof and hydroxypropyl cellulose wherein the ratio of cellulose acetate, cellulose acetate butyrate and combinations thereof to hydroxypropyl cellulose is in the range of about 97/3 to about 50/50; and forming a chewable tablet by compressing the coated medicament in the presence of excipients.

15. A method for taste masking medicaments comprising coating a medicament composition with a taste masking effective amount of a polymer blend of cellulose acetate, cellulose acetate butyrate, or combination thereof and hydroxypropyl cellulose.

16. The method of claim 15 wherein the medicament coated is selected from the group consisting of ibuprofen, aspirin, naproxen, acetaminophen, loperamide, pseudoephedrine, dextromethorphan, chlorpheniramine, diphenhydramine, famotidine, cimetidine, ranitidine, nizatidine, salts thereof, and mixtures thereof.

17. The method of claim 15 wherein the medicament is dexibuprofen lysine.

18. A method of providing sustained release of a medicament comprising coating a medicament with a sustained release effective amount of a polymer blend of cellulose acetate, cellulose acetate butyrate or combination thereof and hydroxypropyl cellulose.

19. The method of claim 18 wherein the medicament is selected from the group consisting of ibuprofen, aspirin, naproxen, acetaminophen, loperamide, pseudoephedrine, dextromethorphan, chlorpheniramine, diphenhydramine, famotidine, cimetidine, ranitidine, nizatidine, salts thereof, and mixtures thereof.

* * * * *